(12) United States Patent
Nazzaro et al.

(10) Patent No.: US 8,790,293 B2
(45) Date of Patent: Jul. 29, 2014

(54) INJECTOR APPARATUS WITH FIXED PLUNGER AND METHOD OF USE

(71) Applicant: pSivida US, Inc., Watertown, MA (US)

(72) Inventors: Martin Nazzaro, Quincy, MA (US); Josh York, Ipswich, MA (US); Ron LeBlanc, Hopedale, MA (US)

(73) Assignee: pSivida US, Inc., Watertown, MA (US)

( * ) Notice: Subject to any disclaimer, the term of this patent is extended or adjusted under 35 U.S.C. 154(b) by 0 days.

(21) Appl. No.: 13/763,587

(22) Filed: Feb. 8, 2013

(65) Prior Publication Data

US 2013/0267931 A1 Oct. 10, 2013

Related U.S. Application Data

(60) Provisional application No. 61/597,264, filed on Feb. 10, 2012.

(51) Int. Cl.
*A61M 31/00* (2006.01)

(52) U.S. Cl.
USPC .................. 604/57; 604/59; 604/506; 606/99

(58) Field of Classification Search
USPC .................. 604/57, 59, 63, 506; 606/99, 107; 623/902, 905–907
See application file for complete search history.

(56) References Cited

U.S. PATENT DOCUMENTS

| | | | | |
|---|---|---|---|---|
| 4,105,030 | A | * | 8/1978 | Kercso .......................... 604/506 |
| 5,284,479 | A | * | 2/1994 | de Jong .......................... 604/60 |
| 7,798,988 | B2 | * | 9/2010 | Aubert et al. .................... 604/57 |
| 7,976,490 | B2 | * | 7/2011 | Lawter et al. .................... 604/63 |
| 8,131,346 | B2 | * | 3/2012 | Chesbrough et al. .......... 600/435 |
| 2004/0260300 | A1 | * | 12/2004 | Gorensek et al. ............... 606/86 |
| 2007/0073265 | A1 | * | 3/2007 | Rue et al. ........................ 604/500 |
| 2009/0281520 | A1 | * | 11/2009 | Highley et al. ................. 604/506 |
| 2009/0299298 | A1 | * | 12/2009 | Bussmann ..................... 604/224 |
| 2012/0165723 | A1 | * | 6/2012 | Horvath et al. .................... 604/9 |

* cited by examiner

*Primary Examiner* — Nicholas Lucchesi
*Assistant Examiner* — Gerald Landry, II
(74) *Attorney, Agent, or Firm* — Foley Hoag LLP

(57) ABSTRACT

Disclosed herein is an injector device for delivering an implant, the device including a retracting element, a cannula needle, and a plunger. The device may comprise an latch that, when actuated by a user, causes the retracting element to move the cannula needle away from the delivery site, allowing the plunger to eject the implant into the site. The device may be configured for intraocular drug delivery.

15 Claims, 3 Drawing Sheets

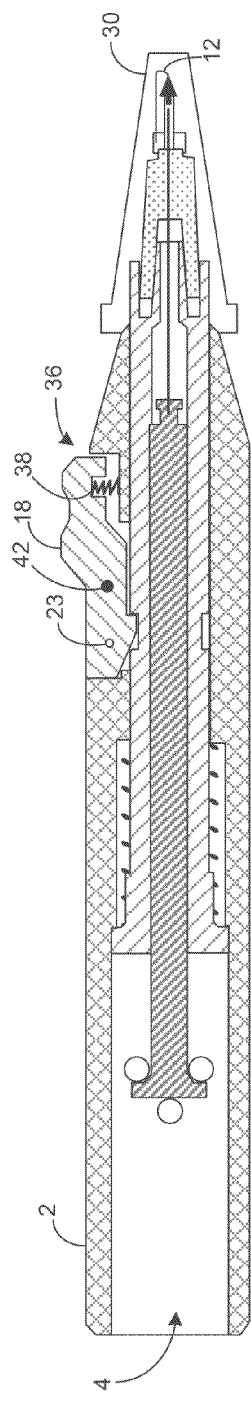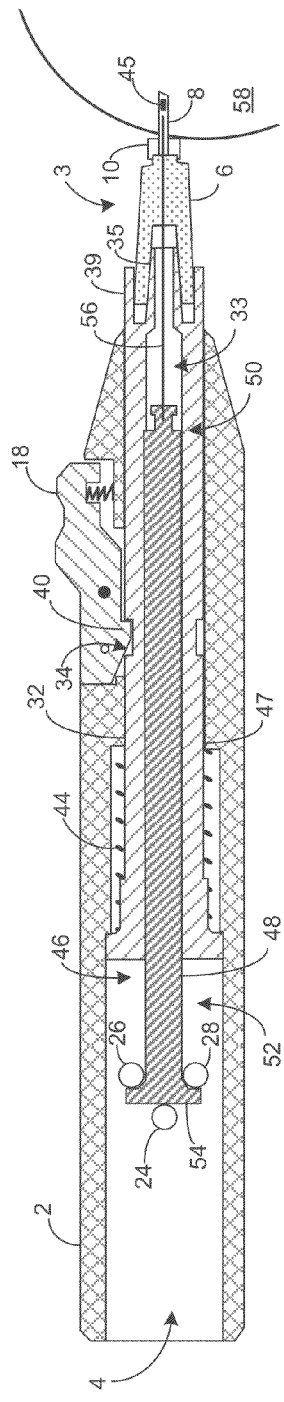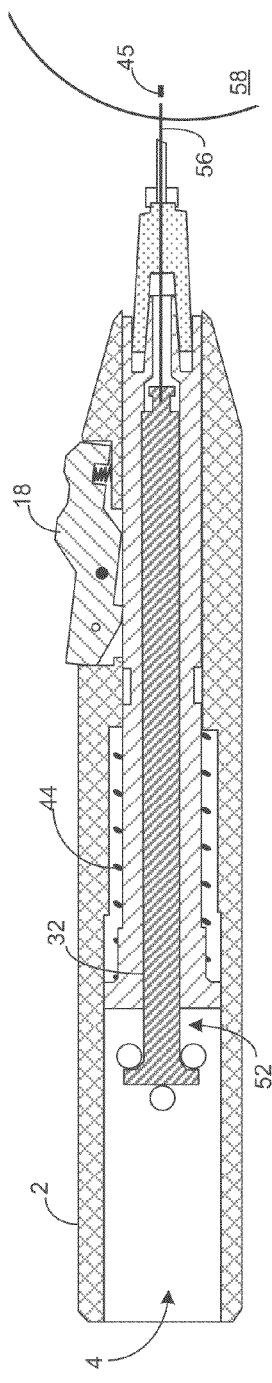

INJECTOR APPARATUS WITH FIXED PLUNGER AND METHOD OF USE

REFERENCE TO RELATED APPLICATION

This application claims the benefit of U.S. Provisional Application No. 61/597,264, filed Feb. 10, 2012, the disclosure of which is incorporated herein by reference thereto.

BACKGROUND OF THE INVENTION

The human eye is a highly evolved and complex sensory organ. Damage to any of its essential structures can result in impairment of vision. Treatments of various eye conditions and diseases often consist of applying doses of appropriate medications in aqueous suspension solutions or ointments. While such treatments are satisfactory for conditions that require only one or a few applications of the medicinal agents, certain conditions require more frequent doses and such treatments are inconvenient to patients. In contrast, ophthalmic medicinal agents in solid implant forms allow a high weight of drug per administered volume. This is particularly advantageous when a large amount of drug must be administered per dose or when the volume is constrained, as in intraocular injections. Additionally, the solid state also renders the compound less sensitive to solution-mediated chemical degradation.

Direct injection into a sensitive and delicate structure like the eye has certain challenges and attendant difficulties. There are a number of procedures and devices that have been developed for the controlled injection of an implant into a tissue, such as an eye. However, improved procedures and devices would be beneficial.

SUMMARY OF THE INVENTION

Disclosed herein is an injector device that delivers an implant into a tissue. In certain embodiments, the injector device is fitted with detachable protectors to secure the device during events such as handling and shipping.

In the present disclosure, the term "proximal" is used to refer to that portion of an element closest to the physician using the device to inject an implant into an injection site. The term "distal" is used herein to refer to that portion of an element farthest from the physician's hand, and closest to the injection site, when the device is utilized to inject an implant. The term "transverse" is used herein to refer to a plane orthogonal to a longitudinal axis of the injector device. The term "injector" is broadly intended to comprise all types of dispensing apparatus that include a hollow shaft and a retracting element. The injector of the present disclosure is not restricted to medical use, and may be utilized for suitable non-medical applications, such as industrial or home usages.

In a first aspect of this invention, the invention relates to an injector device including a syringe barrel defining a central axial cavity and a cannula needle defining a central axial cavity, both central axial cavities in communication. An implant to be delivered to a target tissue site is disposed in the central axial cavity of the cannula needle. A retracting element is coaxially coupled to the proximal end of the cannula needle, and is adapted to retract the cannula needle into the syringe barrel. A plunger is fixedly disposed in the central axial cavity of the syringe barrel. The plunger may be held in place within the syringe barrel by one or more anchor elements disposed near the proximal end of the plunger. When the cannula needle retracts via the retracting element, the plunger extends through the central axial cavity of the cannula needle and beyond the distal end of the syringe barrel, delivering the implant to the target tissue site.

In another aspect of the invention, the injector device described above further includes a latch located on the exterior of the syringe barrel and coupled to the retracting element. When the latch is activated by a physician, the cannula needle retracts, delivering the implant to the target tissue site. The injector device may be equipped with a disengageable latch guard coupled to the latch to prevent activation of the latch while the latch guard is engaged. In some embodiments, the injector device is equipped with one or more protector elements, such as a disengageable block that obstructs the implant from exiting the distal end of the cannula needle during transportation and handling. In some embodiments, the block is a wire having a hook shape, and a first bell-shaped end of the wire caps the distal end of the cannula needle and a second end of the wire is secured to a portion of the injector device.

A stop may be disposed on the cannula needle, the stop having a portion that extends beyond a cross section of the cannula needle. In some embodiments, the stop includes a tubular collar coaxially positioned with the cannula needle, and a positive cross-sectional area difference between the tubular collar and the needle prevents penetration of the cannula needle into a tissue beyond a pre-determined depth.

In another aspect of the invention, the invention relates to a method of injecting an implant using an injector device by first providing an injector device as described herein, inserting the cannula needle of the injector device into a tissue, activating the latch to cause the retracting element to retract the cannula needle from around the implant, and removing the device from the tissue while leaving the implant in the tissue. Additionally, the method may include stopping the insertion of the cannula needle into the tissue when a surface of the tissue contacts a stop disposed on the cannula needle, the stop having a portion that extends beyond a cross section of the cannula needle. Prior to inserting the cannula needle of the injector device into a tissue, the method may include disengaging a block from the injector device, wherein the block obstructs the implant from exiting through the distal end of the cannula needle. This method may be used to inject an implant into eye tissue, e.g., through the sclera of an eye. The cannula needle may be a 25-gauge needle, and may have a beveled tip. In some embodiments, the longitudinal length of the implant is between 0.1 and 0.6 centimeters.

BRIEF DESCRIPTION OF THE DRAWINGS

FIG. 2 depicts a series of longitudinal cross-sectional views of injector device configurations, wherein FIG. 2A depicts an injector device equipped with a set of disengageable protectors coupled thereto, FIG. 2B depicts an injector device in an extended configuration with an implant disposed therein, and FIG. 2C depicts an injector device in a retracted configuration after delivering the implant to a tissue site.

FIG. 6 depicts two disengageable block configurations, wherein

DETAILED DESCRIPTION

The device and method described herein provide an injector device capable of delivering an implant into a tissue. In certain embodiments, the injector device is fitted with disengageable protectors to secure the device during events such as handling and shipping. It will be understood by one of ordinary skill in the art that the device and method described herein can be adapted and modified for other suitable applications and that such other additions and modifications will not depart from the scope hereof.

Figure 1:
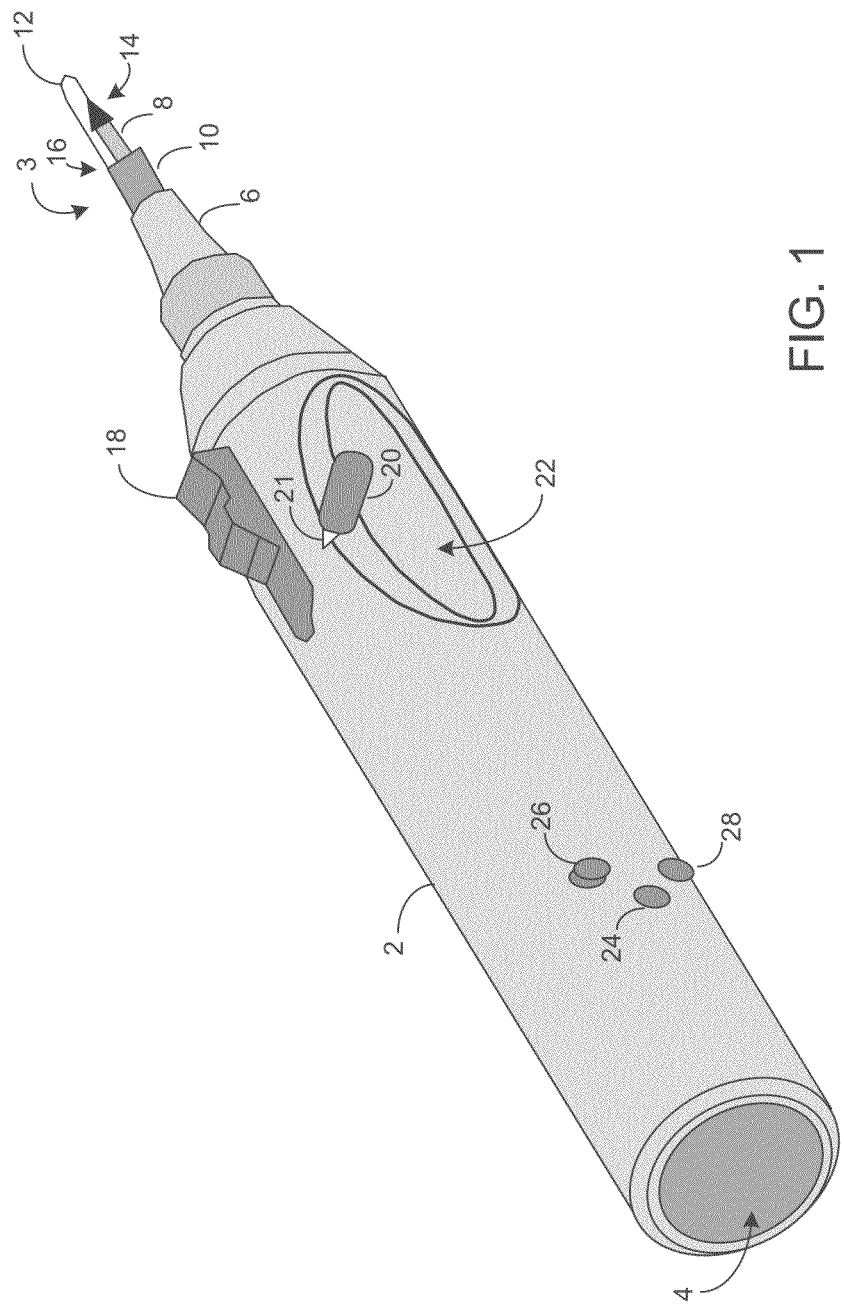
FIG. 1 is a perspective view of an injector device of the present invention.

FIG. 1 is a perspective view of an injector device of the present invention. The injector comprises a syringe barrel 2 with a central axial cavity 4. The central axial cavity 4 may have a circular transverse cross-sectional shape, as shown in the current embodiment, although the cross-sectional shape may be square, triangular, polygonal, or any other suitable shape. Coaxially aligned with the syringe barrel 2 are a cannula needle assembly 3, including a needle hub collar 6 and a cannula needle 8, and a tubular stop 10 disposed around the cannula needle 8. A hook-shaped disengageable block 12 has a first end 14 positioned to cap the distal end of cannula needle 8 and a second end 16 anchored to the needle hub collar 6. A latch 18 is disposed in a slot in the syringe barrel 2, and protrudes from the exterior of the syringe barrel 2. A detachable guard 20 extends through a barrel guard aperture 21 in the syringe barrel 2 and into a latch guard aperture 23 (FIG. 2) of the latch 18. When the guard 20 is positioned within the barrel guard aperture 21 and the latch guard aperture 23, the latch 18 is prevented from being depressed into the syringe barrel 2. The exterior of the syringe barrel 2 includes a concave gripping portion 22 adapted to allow the injector device to be comfortably operated in a physician's hand. The concave gripping portion 22 may be integrally formed from the syringe barrel 2, as shown, or may be mechanically, chemically or otherwise coupled to the syringe barrel 2. Any of a variety of shapes may be selected for the concave gripping portion 22 to provide suitable finger placement during injector device handling. A number of anchor elements 24, 26 and 28 are mounted on the syringe barrel 2 and extend into the central axial cavity 4.

Figure 3:
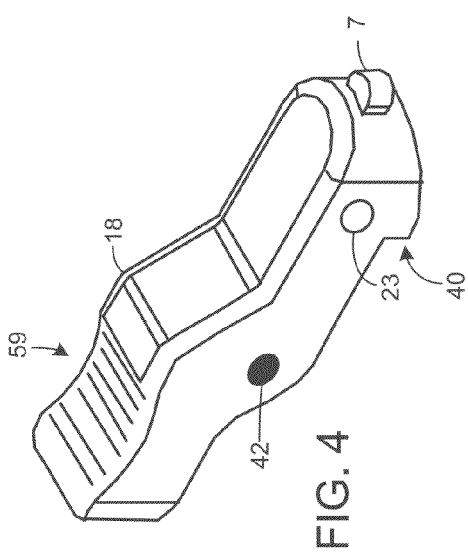
FIG. 3 is a perspective view of a syringe barrel of the injector device of FIG. 2.
Figure 4:
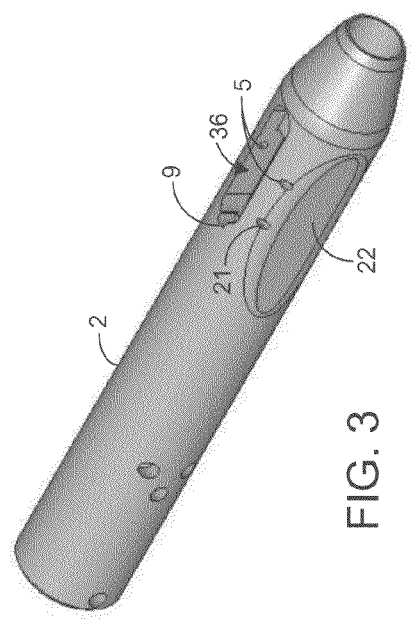
FIG. 4 is a perspective view of a latch of the injector device of FIG. 2.

FIG. 2 depicts a series of longitudinal cross-sectional views of injector device configurations. FIG. 2A depicts an injector device in an extended configuration, additionally equipped with a set of disengageable protectors coupled thereto, including disengageable block 12 and shield 30. Shield 30 is a detachable cap that seats securely on the syringe barrel 2 of the injector device to prevent any damage to the cannula needle assembly 3. The latch 18 is received in a latch slot 36 of the syringe barrel 2. FIGS. 3 and 4 are perspective views of the syringe barrel 2 and the latch 18, respectively. A latch axle (not shown) extends from pivot apertures 5 (FIG. 3) in the syringe barrel 2 and fully or partially through a latch pivot aperture 42 (FIG. 2A) so that the latch 18 can pivot about the latch pivot aperture 42. When the latch 18 is properly disposed in the latch slot 36, a latch tab 7 (FIG. 4) of the latch 18 is positioned in a complementarily-shaped latch tab notch 9 (FIG. 3) in the syringe barrel 2. A latch spring 38 (FIG. 2A) is mounted in the latch slot 36 between the syringe barrel 2 and the latch 18. The latch spring 38 is a helical compression spring, with a height of preferably 0.05"-0.15", and a spring constant of preferably approximately 9 lbs/in. The latch spring 38 may be made of stainless steel or any other suitable spring material.

FIG. 2B also depicts an injector device in an extended configuration, but without the disengageable protectors illustrated in FIG. 2A. In the configuration of FIGS. 2A and 2B, a channel catch 40 of the latch 18 extends into the central axial cavity 4 of the syringe barrel 2 and is seated in a channel 34 of a retracting element 32. The retracting element 32 extends longitudinally within the central axial cavity 4, and is surrounded by a refractor spring 44 along a portion of its length near its proximal end. The proximal end of the retractor spring 44 abuts the contoured proximal end of the retracting element 32, and the distal end of the refractor spring 44 abuts a shoulder 47 of the inner peripheral surface of the syringe barrel 2. Thus, the retractor spring 44 is prevented from sliding distally within the central axial cavity 4 when the injector device is in the extended configuration depicted in FIGS. 2A and 2B. The refractor spring 44 is a helical compression spring, with a height of preferably 0.25"-0.5", and a spring constant of preferably approximately 1 lbs/in. The retractor spring 44 may be made of stainless steel or any other suitable spring material.

Figure 5:
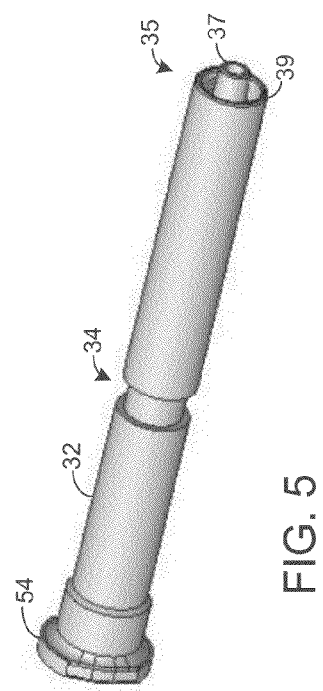
FIG. 5 is a perspective view of a retracting element of the injector device of FIG. 2.

The refracting element 32 defines a central axial cavity 33. For example, in the embodiment depicted in FIG. 5, the refracting element 32 is a hollow cylindrical rod, preferably made of polycarbonate or another such material, with a central axial cavity 33 and machined contours (such as the channel 34), whose shape allows it to fit securely within the central axial cavity 4 of the syringe barrel 2. The distal end 35 of the retracting element 32 includes an inner portion 37 and an outer portion 39, configured to coaxially couple to the needle hub collar 6 at the proximal end of the cannula needle assembly 3. Those of ordinary skill in the art will recognize that a variety of other or additional coupling mechanisms may be used to securely engage the cannula needle assembly 3 to the retracting element 32, such as chemical bonding. In alternative embodiments, the cannula needle assembly 3 may be integrally formed with the retracting element 32.

The cannula needle assembly 3 includes a cannula needle 8 that defines a central axial cavity. The cannula needle 8 may be formed from, for example, between about 18- and 30-gauge tubing (e.g., a 25-gauge needle). The cannula needle 8 may have a beveled tip at its distal end disposed at a pre-determined angular relation to the longitudinal axis of the needle's central axial cavity. Although the cannula needle 8 preferably has a straight longitudinal profile, other suitable longitudinal needle shapes may be used. The needle 8 may be made of any suitably rigid material such as metal or metal alloys; for example, stainless steel or the like. An implant 45 is adapted to fit in the central axial cavity of the cannula needle 8 from its distal end as depicted in FIG. 2B. The implant 45 may be of any solid composition, e.g., for releasing a drug or other agent.

Disposed between the distal end of the needle hub collar 6 and the cannula needle 8 is a stop 10. A positive transverse cross-sectional area difference between the stop 10 and the cannula needle 8 prevents the needle 8 from penetrating a tissue beyond its longitudinal length that extends longitudinally from the stop 10 to the distal end of the cannula needle 8. This longitudinal length is defined as a penetration depth of the needle 8. The stop 10 may be integrally formed with the cannula needle assembly 3 or, in another embodiment, securely coupled to the cannula needle assembly 3. In the present embodiment, the stop 10 comprises a tubular collar or ring coaxially situated between the distal end of the needle hub collar 6 and the distal end of the cannula needle 8. Those of skill in the art will recognize that there are a variety of stop configurations suitable for controlling the penetration depth of the cannula needle 8. A number of exemplary stop configurations are described in Nazarro et al., U.S. Patent Application Publication No. 2008/0071246, incorporated by reference herein in its entirety. In some embodiments, calibration lines may be optionally provided on the cannula needle 8 to visually indicate one or more target penetration depths.

The injector device also includes a plunger 46 disposed in the central axial cavity 4 defined by the syringe barrel 2. The plunger 46 includes a plunger base 48, having a distal end 50 and a proximal end 52. The plunger's transverse cross-sectional shape may vary as long as it fits into the central axial cavity 33 of the retracting element 32. An end-piece 54 at the proximal end 52 may be integrally formed with or securely coupled to the plunger 46. The end-piece 54 is anchored to the syringe barrel 2 by anchor elements 24, 26 and 28. As illustrated in FIG. 2, the end-piece 54 has a "T" shape in profile view, and the three anchoring elements 24, 26 and 28 are disposed within the central axial cavity 4 so as to secure the end-piece 54 at a fixed location and prevent the end-piece 54 from moving longitudinally within the syringe barrel 2. In different embodiments, the shape of the end-piece 54 and the arrangement of one or more anchoring elements may vary as long as the plunger 46 is secured within the syringe barrel 2. The plunger 46 is preferably positioned to not extend beyond the proximal end of the injector device when the device is in an extended configuration.

The plunger 46 also includes a plunger rod 56, having a proximal end coupled to a distal end of the plunger base 48. The plunger rod 56 is positioned within the cannula needle 8 and adapted to eject the embedded implant 45 when the retracting element 32 retracts into the syringe barrel 2. More particularly, the plunger 46 is configured such that the distal end of the plunger rod 56 is close to or beyond the distal end of the cannula needle 8 when the retracting element 32 has retracted into the syringe barrel 2 (as discussed below with reference to FIG. 2C).

When the injector device is in the extended configuration illustrated in FIG. 2B, the latch spring 38 is under compression and exerts an upward force on the distal end of latch 18. Because the latch 18 is pivotally coupled to the syringe barrel 2 about the latch pivot aperture 42, this upward force presses the channel catch 40 into the channel 34 of the refracting element 32. At the same time, the refractor spring 44 is under compression, and applies a leftward force to the retracting element 32. While the channel catch 40 is seated in the channel 34, the retracting element cannot move with respect to the syringe barrel 2. However, if the guard 20 (FIG. 2) is removed, and a sufficient downward force is applied to the distal end of the latch 18 (e.g., at the tactile ridges 59 illustrated in FIG. 4), the upward force exerted by the latch spring 38 is overcome. As a result, the channel catch 40 is disengaged from the channel 34 and the retracting element 32 is pulled leftward by the expansion of the retractor spring 44. As the retracting element 32 moves leftward, the cannula needle assembly 3 retracts partially into the central axial cavity 4 of the syringe barrel 2, as shown in FIG. 2C. The plunger 46 remains in a fixed position relative to the syringe barrel 2 as the retracting element 32 and the cannula needle assembly 3 retract proximally, leaving the distal end of the plunger rod 56 and the implant 45 at the tissue site.

The syringe barrel 2, the concave gripping portion 22, the plunger base 48, the plunger rod 56, the retracting element 32 and the latch 18 can be prepared from hard plastic, glass, stainless steel or other suitably durable materials that may be transparent, translucent, opaque, or non-opaque. All the aforementioned pieces may have the same or different material compositions. For example, the concave gripping portion 22 may or may not be made of the same material as the syringe barrel 2 and the plunger base 48 may or may not have the same material composition as the plunger rod 56. The plunger rod 56 is made of a suitably rigid material, such as stainless steel or hard plastic, so that it can eject an implant 45 from the cannula needle 8 when the retracting element 32 retracts. The latch 18 and syringe barrel 2 are preferably made from ABS plastic. All the above pieces can be prepared from heat- or irradiation-stable materials for reuse or prepared as disposables for single-use applications.

The plunger 46 assumes a shape that allows it to fit securely within the central axial cavity 33 of the retracting element 32. In contrast to plungers utilized in syringes for the injection of liquid, the plunger 46 of the present invention does not need to form an air-tight seal with the inner peripheral surface of the retracting element 32, and in fact, may define passages that permit the free movement of air during use. Similarly, the retracting element 32 need not form an air-tight seal with the inner peripheral surface of the syringe barrel 2.

Figure 6A:
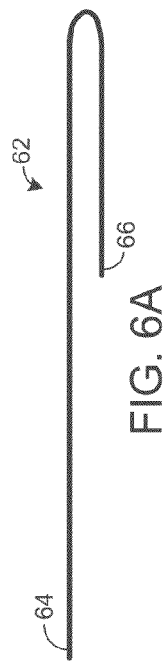
FIG. 6A is a perspective view of a disengageable blocking wire and FIG. 6B is a perspective view of a disengageable blocking cap.
Figure 6B:
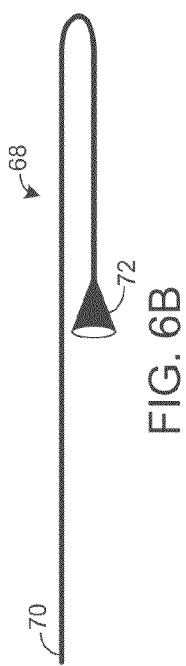

In certain embodiments, a disengageable block 12, which may be made of a suitably rigid material such as stainless steel, hard plastic, or the like, may be utilized to reversibly obstruct the implant 45 from exiting the cannula needle 8 from its distal end as shown in FIG. 2A. FIG. 6 depicts two disengageable block configurations, wherein FIG. 6A is a perspective view of a disengageable blocking wire 62 and FIG. 6B is a perspective view of a disengageable blocking cap 68. The disengageable blocking wire 62 is a hook-shaped element with a first end 64 secured to a portion of the injector device and a second end 66 configured to penetrate the distal end of the cannula needle 8 when the blocking wire 62 is engaged with the injector device. The first end 64 is secured to the injector device by, e.g., a securing member, such as a tubular ring, disposed around a periphery of a portion of the injector device, such as around the needle hub collar 6. The disengageable blocking cap 68 is also a hook-shaped element with a first end 70 secured to a portion of the injector device, but with a second end 72 configured in a bell or cone or similar shape to surround and protect the distal end of the cannula needle 8 when the blocking cap 68 is engaged with the injector device. The disengageable block may be made of any malleable material such as rubber, synthetic rubber, soft plastic, metal, or the like. Additional examples of disengageable blocks that may be used with the present invention are described in Nazarro et al., U.S. Patent Application Publication No. 2008/0071246, incorporated by reference herein in its entirety.

The injector device described above can be prepared by any suitable method, and the various parts assembled in any suitable order. A preferred assembly method includes mounting the latch spring 38 within the latch slot 36 as shown in FIG. 2, and attaching the latch 18 to the syringe barrel 2 by placing the latch 18 into the latch slot 36 and engaging the latch axle in the latch pivot 42. The latch spring 38 is seated in a notch of the latch 18 as shown in FIG. 2. Next, a retractor/spring subassembly is assembled by inserting the distal end of the retracting element 32 into the axial cavity of the retractor spring 44 and sliding the retractor spring 44 toward the proximal end of the retracting element 32. The distal end of the retractor/spring subassembly is then inserted into the proximal end of the central axial cavity 4 of the syringe barrel 2. A rightward force is applied to the proximal end of the retracting element 32 to compress the retractor spring 44 until the channel catch 40 of the latch 18 falls into the channel 34 of the retracting element 32. In this position, the refracting element 32 is latched in place, and the latch guard 20 (FIG. 1) is inserted into the barrel guard aperture 21 (FIG. 1) until it extends through the latch guard aperture 23 in the latch 18 (FIG. 2). With the latch guard 20 in place, the latch 18 cannot be accidentally actuated during the remaining assembly process. Next, the anchoring elements 26 and 28 are mounted within the central axial cavity 4, and the distal end of the plunger 46 is inserted into the syringe barrel 2. The plunger 46 is positioned between the anchoring elements 26 and 28, and within the central axial cavity 33 of the retracting element 32. The remaining anchoring element 24 is mounted to the syringe barrel 2, locking the end-piece 54 of the plunger 46 in place within the central axial cavity 33. Next, at the distal end of the injector device, the distal end of the plunger rod 56 is fitted into the proximal end of the cannula needle assembly 3 and guided into the cannula needle 8. The cannula needle assembly 3 is then coupled to the retracting element 32 as shown in FIG. 2, followed by disposing the implant 45 in the cannula needle 8. The stop 10 can be coupled to the cannula needle 8 after the cannula needle assembly 3 is coupled to the retracting element 32, or as part of the cannula needle assembly process. Optionally, the above method may include fitting the protecting elements such as the disengageable block 12 and the shield 30, optionally fitting one end of the hook-shaped block 12 to the distal end of the cannula needle 8 and securing a second end of the block 12 to the needle hub collar 6 of the cannula needle assembly 3.

The injector device may be employed by first removing the shield 30, the block 12 and the latch guard 20 if they are present, inserting the cannula needle 8 into a tissue to a depth where the stop 10 contacts the surface of the tissue, then depressing the latch 18 into the syringe barrel 2 to cause the retracting element 32 to retract into the syringe barrel 2 and leave the implant 45 into the tissue site.

In one embodiment of the injector device, the device is designed to deliver a drug to an eye 58 (FIG. 2). In particular, the cannula needle 8 of the injector device is adapted to penetrate a sclera of the eye 58. The cannula needle 8 may be a straight 25-gauge cannula needle and have, for example, a beveled tip at its distal end, e.g., disposed at an angle of about between 10 and 13 degrees, preferably about 11.5 degrees, in relation to the longitudinal axis of the needle's central axial cavity. The stop 10 of the depicted device comprises a tubular collar that is coaxially coupled to the cannula needle assembly 3, wherein the cannula needle 8 is disposed and situated in such a manner that its penetration depth 507 is about 0.25 to 0.35 cm. The implant 45 may have a longitudinal length of about 0.1 to 0.9 cm.

Thus, the invention generally provides an injector device with a retracting element for delivering an implant to a tissue site. The purpose of the above description and examples is to illustrate some non-limiting embodiments of the present invention. It will be apparent to those skilled in the art that various modifications and variations may be made to the device and method of the present invention without departing from the spirit or scope of the invention. All publications and patents cited herein are hereby incorporated by reference in their entirety.

What is claimed is:

1. An injector device comprising:
a syringe barrel defining a central axial cavity, and having a distal end and a proximal end;
a cannula needle having a distal end and a proximal end and defining a central axial cavity in communication with the central axial cavity of the syringe barrel;
a retracting element coaxially coupled to the proximal end of the cannula needle adapted to retract the cannula needle into the syringe barrel;
a plunger having a distal end and a proximal end, disposed in the central axial cavity of the syringe barrel at a fixed position therein, and, when the cannula needle retracts, extending through the central axial cavity of the cannula needle and beyond the distal end of the syringe barrel; and
an implant disposed in the central axial cavity of the cannula needle between the plunger rod and the distal end of the needle.

2. The injector according to claim 1, wherein the device further comprises a disengageable block that obstructs the implant from exiting the distal end of the cannula needle.

3. The injector according to claim 1, further comprising a latch located on the exterior of the syringe barrel and coupled to the retracting element such that when the latch is activated, the cannula needle retracts.

4. The injector according to claim 1, further comprising a stop disposed on the cannula needle and having a portion that extends beyond a cross section of the cannula needle.

5. The injector of claim 4, wherein the stop includes a tubular collar coaxially positioned with the cannula needle, and a positive cross-sectional area difference between the tubular collar and the needle prevents penetration of the cannula needle into a tissue beyond a pre-determined depth.

6. The injector according to claim 1, further comprising one or more anchor elements at the proximal end of the plunger to hold the plunger in place.

7. The injector according to claim 3, further comprising a disengageable latch guard coupled to the latch to prevent activation of the latch while the latch guard is engaged.

8. The injector according to claim 2, wherein the block is a wire having a hook shape, and a first bell-shaped end of the wire caps the distal end of the cannula needle and a second end of the wire is secured to a portion of the injector device.

9. A method of injecting an implant using an injector device, comprising:
providing an injector device of claim 3;
inserting the cannula needle into a tissue;
activating the latch to cause the retracting element to retract the cannula needle from around the implant; and
removing the device from the tissue while leaving the implant in the tissue.

10. The method of claim 9, wherein the tissue is an eye.

11. The method of claim 9, wherein the cannula needle is a 25-gauge needle.

12. The method of claim 9, wherein the cannula needle has a beveled tip adapted to penetrate a sclera of an eye.

13. The method according to claim 9, wherein a longitudinal length of the implant is between 0.1 to 0.6 centimeters.

14. The method of claim 9, wherein the device further comprises a stop disposed on the cannula needle, the stop having a portion that extends beyond a cross section of the cannula needle, whereby the insertion of the cannula needle into the tissue is stopped when a surface of the tissue contacts the stop.

15. The method of claim 9, wherein the device further comprises a disengageable block that obstructs the implant from exiting the distal end of the cannula needle, and wherein the method further comprises disengaging the block from the injector device prior to inserting the cannula needle into the tissue.

* * * * *